United States Patent [19]

Abrahams

[11] Patent Number: 4,491,591
[45] Date of Patent: Jan. 1, 1985

[54] ANTITHROMBOTIC AGENT

[75] Inventor: Sanders L. Abrahams, Raleigh, N.C.

[73] Assignee: Burroughs Wellcome Co., Research Triangle Park, N.C.

[21] Appl. No.: 512,910

[22] Filed: Jul. 12, 1983

[30] Foreign Application Priority Data

Jul. 16, 1982 [GB] United Kingdom ............... 8220651

[51] Int. Cl.³ ............................................. A61K 31/40
[52] U.S. Cl. ................................................ 424/274
[58] Field of Search ....................................... 424/274

[56] References Cited

U.S. PATENT DOCUMENTS 4,012,495 3/1977 Schmiechen et al. ............ 424/274

Primary Examiner—Frederick E. Waddell
Attorney, Agent, or Firm—Donald Brown

[57] ABSTRACT

A method of treatment of thrombo-embolic conditions in a mammal including man comprising the administration of a non-toxic effective amount of the compound of Formula (I) is described:

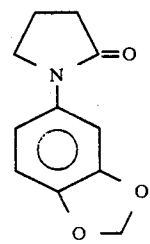

(I)

Preferred formulations include those suitable for oral, rectal or parenteral administration, and the preferred dose is in the range of from 1 to 120 mg per kg body weight of the compound per day.

3 Claims, No Drawings

ANTITHROMBOTIC AGENT

This invention relates to a compound useful in medicine as an antithrombotic agent.

Platelets, the smallest formed elements of the blood, play an important role in hemostasis by stopping the outward flow of blood through ruptures in the blood vessel wall. They aggregate or fuse together at the site of injury to form a temporary plug or clot which seals the blood vessel. The clumping together of the platelets initiates a chain of biochemical reactions which leads to the reinforcing of the clot with the fibrous protein, fibrin.

Aggregation of platelets appears to be triggered by their contact with certain surfaces, such as the basement membranes of the blood vessels or collagen fibrils. Once aggregation has begun, the platelets stick to each other.

It is clear that the ability of platelets to aggregate and initiate thrombus formation is important to protect the organism from excessive loss of blood as a result of injury. However, in some individuals, platelets will begin to adhere to the inner walls of the blood vessels as a result of a disease process. As more platelets accumulate, a blood clot may form which restricts the amount of blood flowing through the vessel. This can result in the interruption of blood flow to a vital organ such as the heart, for example, thereby causing a heart attack. A thrombus formed in this way may also become disloged and travel as an embolus through the circulatory system. In such a case, there is a risk that the embolus could become lodged in vessels supplying organs such as the brain or lung and could restrict the flow of blood so much that the function of these organs would be severly impaired. This could be fatal or render the individual disabled.

Further general discussions of blood platelets are presented by S. B. Kahn, American Family Physician, Vol. 21 No. 5, 166, (1980) and M. B. Zucker, Scientific American, Vol. 242, p. 86, June (1980) and Vol 204, p. 58, February (1961).

It is clear from the foregoing discussion that it is desirable under some situations to reduce or prevent the aggregation of blood platelets in vivo in order to avoid the pathological disturbances to the cardiovascular system noted above.

In particular, the present invention relates to compounds of Formula (I).

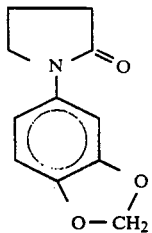

(I)

The compound of formula (I), chemically named 1-(1,3-Benzodioxol-5-yl)-2-pyrrolidinone is useful for inhibiting platelet aggregation in the blood of mammals, including humans, and the treatment of prophylaxis of thrombo-embolic conditions in a mammal including humans, such conditions including those whose Formula (I) has been found, when it is desired to inhibit platelet aggregation, to prevent the formulation of thrombi in mammals, including man. For example these compounds would be useful in prevention of myocardial infarctions, transient ischemic attacks (TIA's), stokes, post-operative thrombosis (including that incurred after artifical heart valve or hip replacement), central retinal vein occlusions and the atheroscelerotic process that leads to a variety of conditions including peripheral vascular diseases and renal vascular hypertension. Other treatable conditions include diabetic retinopathy, thrombotic thrombocytopenia purpura and migraine. Compound I would be useful in maintaining A-V shunt patency in uremic patients maintained on hemodialysis.

It may also be used as additives to blood, blood products, blood substitutes, and other fluids which are used in artificial extra-corporeal circulation system and perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking may be avoided by the presence of the compound of Formula (I).

The amount of Compound (I), required for use in the above conditions will, of course, vary both with the route of administration, the condition under treatment, and the mammal undergoing treatment, but is ultimately at dose of Compound (I) for a mammal is in the range of from 1 to 120 mg per kilogram bodyweight per day; a typical dose for a human recipient being 15 mg/kg body weight per day.

The desired dose is preferably presented as between two and four subdoses administered at appropriate intervals throughout the day. Thus where three sub-doses are employed each will lie in the range of from 1 to 20 mg (base)/kg body weight; a typical dose from a human recipient being 3 mg (base)/kg body weight.

While it is possible for the active compound to be administered alone as the raw chemical, it is preferable to present the active compound as a pharmaceutical formulation. Formulations of the present invention, both for veterinary and for human medical use, comprise the active compound together with one or more pharmaceutically acceptable carriers thereof and optionally any other therapeutic ingredients. The carrier(s) must be pharmaceutically acceptable in the sense of being compatible with the other ingredients of the formulation and not deleterious to the recipient thereof. The other therapeutic ingredient(s) may include other analgesics, anti-inflammatories or antipyretics.

The formulations include those suitable for oral, rectal or parenteral (including subcutaneous, intramuscular and intravenous) administration.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier or both and then, if necessary, shaping the product into the desired formulations.

Formulations of the present invention suitable for oral administration may be presented as discrets units such as capsules, cachets, tablets or lozenges, each containing a predetermined amount of the active compound; as a powder or granules; or a suspension in an aqueous liquid or non-aqueous liquid such as a syrup, an elixir, an emulsion or a draught. The active compound may also be presented as a bolus, electuary or paste.

A tablet may be made by compression or moulding, optionally with one or more accessory ingredients. Compressed tablets may be prepared by compressing in a suitable machine, the active compound being in a free-flowing form such as a powder or granules, optionally mixed with a binder, lubricant, inert diluent, surface active or dispersing agent. Moulded tablets may be made by moulding in a suitable machine, comprising a mixture of the powdered active compound with any suitable carrier.

A syrup may be made by adding the active compound to a concentrated, aqueous solution of a sugar for example sucrose to which may also be added any accessory ingredient. Such accessory ingredient(s) may include flavour-ings, an agent to retard crystallization of the sugar or an agent to increase the solubility of any other ingredient, such as a polyhydric alcohol for example glycerol or sorbitol.

Formulations for rectal administration may be presented as a suppository with a usual carrier such as cocoa butter.

Formulations suitable for parenteral administration conveniently comprise a sterile aqueous preparation of the active compound which is preferably isotonic with the blood of the recipient.

In addition to the aforementioned ingredients, the formulations of this invention may further include one or more accessory ingredient(s) selected from diluents, buffers, flavouring agents, binders, surface active agents, thickeners, lubricants, preservatives (including antioxidants) and the like.

Compound (I) may be prepared by any method known in the art for the preparation of compound of analogous structure.

(1) A method for preparing compound (I) comprises cyclisation, as hereinafter described, of a compound of formula (II) or a compound of formula (III):

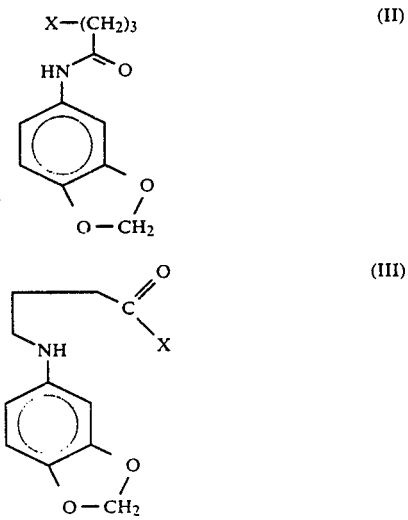

wherein X is a standard leaving group (J. March, Advanced Organic Chemistry, 2nd Ed., page 187, New York (1977)) such as halide for example chloride or bromide, hydroxide, —$OR^1$, imidazolyl, sulphoxonium or tosyl; and $R^1$ is hydrogen or alkyl of 1 to 4 carbon atoms, preferably ethyl. Preferred compounds of formula (II) are those wherein the leaving group is a halide (such as chloride or bromide), hydroxide or tosyloxy, and preferred compounds of formula (III) are those wherein the leaving group is —OR as defined. A particularly preferred method comprises cyclisation of a compound of formula (II) as hereinbefore defined, especially wherein X is chloride.

Cyclisation may be effected at room temperature or with heating for example at a temperature of 155°–220° C., optionally in an oxygen-free atmosphere for example in nitrogen, optionally in an inert solvent such as tetrahydrofuran, dichloromethane, diethyl ether, tert-butanol, xylenes, or toluene, and optionally with a catalyst. The catalyst chosen will depend on the compound of formula (II) or (III) to be cyclised, for example, where the reaction involves elimination of an acid such as hydrochloric, a basic catalyst may be used with or without a solvent such as water or an alcohol such as butanol optionally, but preferably, in the presence of a phase transfer catalyst such as triethylbenzyl ammonium chloride with or without a solvent such as dichloromethane, diethyl ether, xylenes or toluene, but preferably dichloromethane. Examples of suitable basic catalysts are: an alkali metal hydride, hydroxide or alkoxide such as potassium or sodium hydride, potassium or sodium hydroxide, potassium tert-butoxide or lithium di-isopropylamide. The most preferred method of cyclisation is effected by using aqueous sodium hydroxide in the presence of triethylbenzyl ammonium chloride at room temperature.

Where X is a slow or poor leaving group cyclisation may take place by conversion in situ to a further or better leaving group. For example where X is hydroxide, tosyl chloride may be present in the reaction mixture in order that the tosyloxy group (a better leaving group) is substituted for the hydroxide group thereby causing cyclisation to proceed faster and more completely.

EXAMPLE 1

Preparation of 1-(1,3-Benzodioxol-5-yl)-2-pyrrolidinone

4-Chlorobutyryl chloride (1095.5 g, 7.77 mole) was added at 10°–25° C. to a mixture of 3,4-(methylenedioxy)aniline (1000.0 g, 7.29 mole), triethylamine (749.0 g, 7.40 mole) and methylene chloride (25000 mL). After stirring for 18 hours at ambient temperature ether was added and the butyramide intermediate was filtered then reslurried in water. The damp butyramide was combined with methylene chloride (10 L), 50% w/w aqueous sodium hydroxide (2000.0 g, 25.0 mole) and benzyltriethylammonium chloride (50.0 g, 0.22 mole). After stirring for 2.5 hours at ambient temperature the mixture was diluted with water and the aqueous layer was then separated. The methylene chloride layer was washed with water, decolorized with Darco G-60 and Filtrol #19, then vacuum concentrated. Ether was added to the concentrate. The mixture was chilled and the solids were collected and recrystallized from methylene chloride/ether giving 2245.0 g (75), m.p. 89°–91° which was one spot on tlc analysis.

Elemental analysis: Calcd. for $C_{11}H_{11}NO_3$: C, 64.38%; H, 5.40%; N, 6.83%. Found: C, 64.30%; H, 5.33%; N, 6.81%.

EXAMPLE 2

Pharmaceutical Formulations

A. Capsule

| Ingredient | Amount per capsule (mg) |
| --- | --- |
| Compound I | 325.0 |
| Lactose | 174.0 |
| Corn Starch | 174.0 |
| Stearic Acid | 2.0 |

The finely ground active compound was mixed with the powdered excipients lactose, corn starch and stearic acid and packed into gelatin capsule.

B. Tablet

| Ingredient | Amount per tablet (mg) |
| --- | --- |
| Compound | 325.0 |
| Lactose | 125.0 |
| Corn Starch | 50.0 |
| Polyvinylpyrrolidone | 3.0 |
| Stearic acid | 1.0 |
| Magnesium stearate | 1.0 |

The active compound was finely ground and intimately mixed with the powdered excipients lactose, corn starch, polyvinylpyrrolidone, magnesium stearate and stearic acid. The formulation was then compressed to afford one tablet weighing 250 mg.

C. Suppository

| Ingredient | Amount per suppository |
| --- | --- |
| Compound I | 325.0 mg |
| Cocoa Butter, q.s. | 2.0 g | or Wecobee Base (trade name of a hydrogenated carboxylic acid).

EXAMPLE 3

Inhibition of Platelet Aggregation

Ex vivo studies: The aggregation of platelets taken from animals dosed by the oral route with Compound (I) is inhibited when tested with arachidonate and collagen by the method of Born ((1962) Nature 194, 927-929). The dose range required to inhibit aggregation rate by 50% (ED) at 1 hour was 25-35 mg/Kg in guinea pigs. By comparison, the ED for aspirin in the guinea pig was 30 mg/kg.

I claim:

1. A method of inhibiting platelet aggregation in the blood of a mammal comprising the addition of an effective platelet aggregation inhibiting amount of the compound of Formula (I)

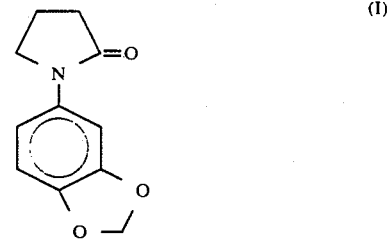

to said blood.

2. A method of claim 1 wherein a mammal is a human.

3. A method of claim 1 wherein the blood is an artificial extra-corporeal circulation system.